US008865950B2

(12) United States Patent
Abba et al.

(10) Patent No.: US 8,865,950 B2
(45) Date of Patent: Oct. 21, 2014

(54) OLEFIN HYDRATION PROCESS WITH AN INTEGRATED MEMBRANE REACTOR

(75) Inventors: Ibrahim Abba, Dhahran (SA); Aadesh Harale, ABQ (SA); Stephan Ralf Vogel, Dhahran Hills (SA); Wei Xu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 493 days.

(21) Appl. No.: 13/207,122

(22) Filed: Aug. 10, 2011

(65) Prior Publication Data

US 2013/0041186 A1    Feb. 14, 2013

(51) Int. Cl.
*C07C 29/04*     (2006.01)
*B01J 8/02*      (2006.01)
*C07C 29/76*     (2006.01)
*B01J 8/00*      (2006.01)

(52) U.S. Cl.
CPC .............. *B01J 8/009* (2013.01); *B01J 8/0257* (2013.01); *C07C 29/76* (2013.01); *B01J 2208/00274* (2013.01); *C07C 29/04* (2013.01); *B01J 8/0278* (2013.01)
USPC ........... 568/896; 568/895; 568/897; 568/898; 568/899; 568/900; 568/901; 568/913

(58) Field of Classification Search
CPC ..................................................... C07C 29/04
USPC ......................................... 568/895–901, 913
See application file for complete search history.

(56) References Cited

U.S. PATENT DOCUMENTS

| | | |
|---|---|---|
| 2,477,380 A | 7/1949 | Kreps et al. |
| 3,994,983 A | 11/1976 | Webers et al. |
| 4,405,409 A | 9/1983 | Tusel et al. |
| 4,547,530 A | 10/1985 | McCreedy et al. |
| 4,579,984 A | 4/1986 | Neier et al. |
| 4,774,365 A | 9/1988 | Chen et al. |
| 4,876,403 A | 10/1989 | Cohen et al. |
| 5,110,478 A | 5/1992 | Haag et al. |
| 5,146,009 A | 9/1992 | Cohen et al. |
| 5,208,387 A | 5/1993 | Harandi et al. |
| 6,228,147 B1 | 5/2001 | Takahashi |
| 6,919,062 B1 | 7/2005 | Vasileiadis et al. |
| 7,141,707 B2 | 11/2006 | Beckmann et al. |
| 7,622,086 B2 | 11/2009 | Takahashi et al. |
| 7,670,394 B2 | 3/2010 | Boe et al. |
| 2002/0099246 A1 | 7/2002 | Ziaka-Vasileiadou et al. |
| 2007/0053811 A1 | 3/2007 | Tsotsis et al. |
| 2009/0057224 A1 | 3/2009 | Huang et al. |
| 2010/0304953 A1 | 12/2010 | Liu et al. |

FOREIGN PATENT DOCUMENTS

| | | |
|---|---|---|
| EP | 0579153 A2 | 1/1994 |
| WO | 8805768 A1 | 8/1988 |
| WO | 9535161 A1 | 12/1995 |

OTHER PUBLICATIONS

Lapkin et al., "A porous carbon membrane reactor for the homogeneous catalytic hydration of propene", Chemical Engineering Science 57 (2002) pp. 2357-2389. Elsevier Science Ltd.
Vane, Leland M., "A review of pervaporation for product recovery from biomass fermentation processes", Journal of Chemical Technology and Biotechnology 80:603-629 (2005), John Wiley & Sons, Ltd.
Dixon, Anthony G., "Recent Research in Cataytic Inroganic Membrane Reactors", International Journal of Chemical Reactor Engineering, vol. 1, (2003), Review R6.
International Search Report and Written Opinion issued Oct. 16, 2012 in PCT/US2012/047003 (8 pages).

*Primary Examiner* — Elvis O Price
(74) *Attorney, Agent, or Firm* — Bracewell & Giuliani LLP; Constance G. Rhebergen; James M. Sellers (57) ABSTRACT

An olefin hydration process and reactor are provided, wherein an integrated membrane selectively removes alcohol product from the reactor, thereby allowing for increased yields.

16 Claims, 4 Drawing Sheets

OLEFIN HYDRATION PROCESS WITH AN INTEGRATED MEMBRANE REACTOR

FIELD OF THE INVENTION

This invention relates to a process for the production of alcohols from olefins. More specifically, the invention relates to an integrated process utilizing a membrane reactor for the production of alcohols from olefins.

BACKGROUND OF THE INVENTION

The hydration of olefins to alcohols in general, and specifically the hydration of butenes to butanols, are commercially important reactions as the alcohol products find several important industrial applications. Hydration reactions are normally acid catalyzed reactions. Because olefins generally have very low solubility in water, relatively strong acids are often required to achieve the desired kinetics for the reaction. The use of strong acids, however, is typically sought to be avoided as the acids can be highly corrosive to the reactor and associated equipment and the processes for acid re-concentration and aqueous waste treatment can be energy demanding.

One preferred technology for hydrations includes the use of thermally stable solid catalysts. Cationic exchange resins and zeolite are important solid catalysts for olefin hydration because it eliminates the use of strong aqueous acids. Cationic exchange resins are known to offer substantial reaction rates in both polar and non-polar media. The use of sulfonated polystyrene resins cross-linked with divinyl benzene as catalysts for the hydration of olefins, such as propylene or butene, has been generally described in the literature (see e.g., U.S. Pat. No. 4,579,984 and U.S. Pat. No. 2,477,380; and references cited therein). While the cationic exchange resins offer several desired advantages, such as ease in separation, and providing non-corrosive environment, the corresponding conversion rates are low. The corresponding olefin rate with solid catalyst (such as the cationic exchange resin) is quite low, typically reported as less than 10% olefin converted by a single pass. Therefore, the need exists to develop a new solid catalyst process that overcomes the equilibrium limitations described above and provides a significantly increased olefin conversion.

SUMMARY

This invention relates to the hydration of olefins to alcohols.

In one aspect, a reactor for the catalytic hydration of olefins is provided. The reactor includes a catalytic reaction zone separated by a permeable membrane, said membrane separating the catalytic reaction zone into permeate and retentate sides of the reaction zone, wherein the retentate side includes an olefin hydration catalyst. The reaction includes a first outlet configured for the removal of fluids from the permeate side of the reaction zone; and a second outlet configured for the removal of fluids from the retentate side of the reaction zone. The permeable membrane is operable to selectively remove at least one olefin hydration product.

In another aspect, a process for the hydration of olefins to produce alcohols is provided. The process includes the steps of contacting an olefin feedstock and water in a reaction zone at reaction conditions sufficient to produce an alcohol product, wherein said reaction zone includes an olefin hydration catalyst, and selectively removing at least a portion of the alcohol product from the reaction zone with a permeable membrane that is selective for the passage of alcohols, wherein the step of removing a portion of the alcohol product shifts the reaction equilibrium.

DETAILED DESCRIPTION OF THE INVENTION

Although the following detailed description contains many specific details for purposes of illustration, it is understood that one of ordinary skill in the art will appreciate that many examples, variations and alterations to the following details are within the scope and spirit of the invention. Accordingly, the exemplary embodiments of the invention described herein and provided in the appended figures are set forth without any loss of generality, and without imposing limitations, relating to the claimed invention.

As used herein, the following terms shall have the following meanings.

Pervaporation shall refer to a membrane process of liquid separation where a liquid mixture (feed stream) is in contact with one side of a selectively permeable membrane, and the components that penetrate through the membrane (the permeate stream) are removed as vapor from the opposite side of the membrane. In the pervaporation process, a heated liquid phase mixture containing at least two components is typically fed to a membrane that has a higher permeation flux for at least one of the components in the feed mixture. The driving force for permeation of the two components is the difference in partial pressure of the feed side and the permeate side of the membrane. Therefore, the permeate side of the membrane is maintained under vacuum or at a lower pressure. The majority of the more highly permeable component and a small fraction of less highly permeable component permeate (or pervaporate) the membrane in the vapor phase, resulting in the cooling of the feed mixture. This is due, at least in part, to the phase change associated with pervaporation across the membrane. The feed mixture is typically reheated to increase the driving force, before it is directed to the next membrane module.

Vapor Permeation refers to a process wherein a pressurized and heated vapor phase mixture containing at least two components is fed to a membrane that has a higher permeation flux, for at least one of the components in the feed mixture. The driving force for permeation of the components is the difference in partial pressure between the feed side and the permeate side of the membrane. Therefore, the permeate side of the membrane is maintained under vacuum or lower pressures. The majority of the more permeable component and a small fraction of less permeable component permeate the membrane in the vapor phase. Because there is no phase change within the membrane module and the operating pressures are usually low, the feed, retentate, and permeate temperatures are essentially the same.

Inorganic Membrane refers to a device that selectively permits the separation of one or more materials from a liquid or gas. Inorganic membranes are versatile as they can operate at elevated temperatures, for example, with metal membranes that are stable at temperatures ranging from 500-800° C., or with ceramic membranes that are stable at temperatures over 1000° C. Inorganic membranes can also be much more resistant to chemical attack, due in part to the wide variety of materials that may be used in the fabrication of inorganic membranes, providing resistance to corrosive liquids and gases, even at elevated temperatures.

Polymeric Membrane refers to a dense-type of membrane that transports species through the hulk of the material. Depending on their state, polymeric membranes can be subdivided into glassy polymeric membranes (prepared at temperatures below the glass transition temperature) and rubbery polymeric membranes (prepared at temperatures above the glass transition temperature). Glassy polymeric membranes have relatively high selectivity and low flux, whereas rubbery polymeric membranes have increased flux and a corresponding lower selectivity. Polymeric membranes can be produced using the phase inversion method. Typical operating temperatures are less than about 90-100° C.

Multistage Process refers to an olefin conversion unit that may also include one or more intermediate reaction zones interposed between a first and second reaction zone. These optional intermediate reaction zones can be operated in a manner that facilitates production of alcohol(s).

Liquid Acids and Solid Acids, when used in reference to liquid catalyst, refers to a water soluble acid, such as $H_2SO_4$, $H_3PO_4$ and other heteropoly acids. Solid catalyst refers to water insoluble catalyst, such as ionic exchange resins, zeolites in acidic forms, and acids supported on solid carriers.

In one embodiment, the present invention relates to a novel membrane reactor that provides an integrated olefin hydration process. More particularly, the present invention provides a membrane reactor for the integrated conversion of olefin to alcohols in the presence of a solid acidic catalyst, wherein the alcohols are simultaneously removed from the reactor with an alcohol selective membrane.

Figure 1:
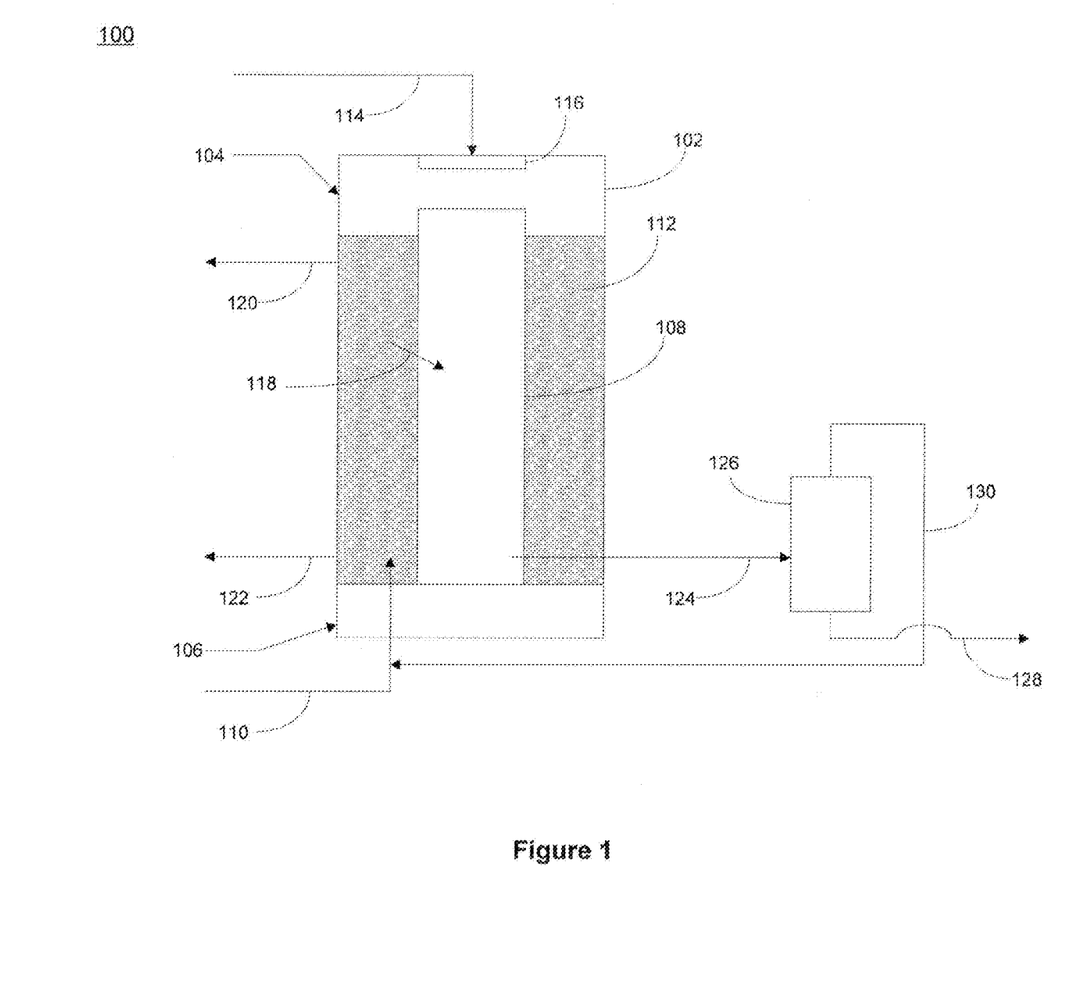
FIG. 1 is a schematic of one embodiment of the invention.

One embodiment of the present invention is provided in FIG. 1. In FIG. 1, reactor 100 having an organic selective membrane is provided. Reactor 100 includes reactor shell 102, upper end 104, lower end 106, and membrane tube 108 positioned vertically within the reactor shell. Olefin feedstock, for example butenes, are supplied to catalyst bed 112 via olefin supply line 110. Water is supplied to the catalyst bed via water supply line 114, and can be supplied to optional water spray head 116. Water spray head 116 facilitates the supply of water to the top of catalyst bed 112, thereby allowing for even distribution of the water to the catalyst bed.

The olefin feedstock can be any lower olefin feedstock (i.e., a feedstream of alkenes having 6 or fewer carbon atoms, preferably between 3 and 5 carbon atoms). In certain embodiments a pure feedstock may be used. In alternate embodiments, a mixed olefin stream, such as a stream that includes mixed butenes, can be used. In certain other embodiments, a mixed streams that includes olefins of various different lengths, for example, propene and butene(s), can be used. Thus, in certain embodiments, a mixed olefin stream obtained from an alternate separation process can be supplied directly to the olefin hydration reactor of the present invention, such as an FCC (fluid catalytic cracking) unit, an enhanced-FCC unit, or a steam cracking unit.

The reaction temperature can be between about 50° C. and 250° C. In certain embodiments, the temperature is between about 70° C. and 200° C. Alternatively, the temperature is between about 80° C. and 150° C. The reactor pressure can be between about 5 and 100 bar, alternatively between about 10 and 80 bar, or alternatively between about 20 and 70 bar.

Membrane tube 108 is an alcohol selective tube, which is operable to allow alcohols to pass through the membrane, while at the same time preventing the catalyst, water and olefins from passing. While shown and described as a tube, it is understood that the membrane apparatus can be formed of many shapes other than cylindrical. Flow of the alcohols through the membrane tube is show by arrow 118. An organic phase that includes olefins, water and alcohol can be collected from the upper portion of the catalyst bed via line 120. Preferably, the organic phase consists mostly of olefins, and has a very minor amount of alcohol and water present. Similarly, an aqueous phase that includes water, olefin and alcohol, preferably mostly water, can be collected via line 122.

Product stream 124, which consists of the converted alcohol and a small fraction of the feed olefin is supplied from membrane tube 108 to separator 126, where the alcohol and olefin are separated. Alcohol is removed from separator 126 via line 128, and olefin is removed via line 130, which can be recycled to the reactor, and combined, for example, with the olefin feed in olefin supply line 110.

The membrane is a selective membrane that allows the passage of certain organic compounds therethrough, such as alcohols. In certain preferred embodiments, the membrane is selective for the passage of certain alcohols, such as alcohols having less than 6 carbon atoms. In certain embodiments, the membrane preferably does not allow the passage of non-organic compounds, such as water or certain gasses, such as hydrogen or nitrogen gas. In certain embodiments, certain non-alcohol compounds, such as aromatic compounds or olefins, are not readily permeable through the membrane. In certain other embodiments, the membrane is selective to organics, including both alcohols and olefins, and prevents the passage of water therethrough. Exemplary membranes includes inorganic membranes based upon zeolites (for example, Silicalite-1, Ge-ISM-5, B-type, or ZSM-11), or polymer based membranes (based upon various polymers, such as, polyimides, polystyrene, polyesters, PTMSP, PVDF, PDMS, and the like).

The removal of the alcohol from the reaction zone causes a shift in the reaction equilibrium, thereby increasing the production of alcohols. The removal of the alcohol product as it is produced thereby allows the reaction to proceed beyond the typical equilibrium point for normal operating conditions. Total reaction yields of alcohol products produced in this hydration reaction show a noticeable increase in overall yields as compared with similar reactions run in reactors that do not include the selective membrane described herein.

Figure 2:
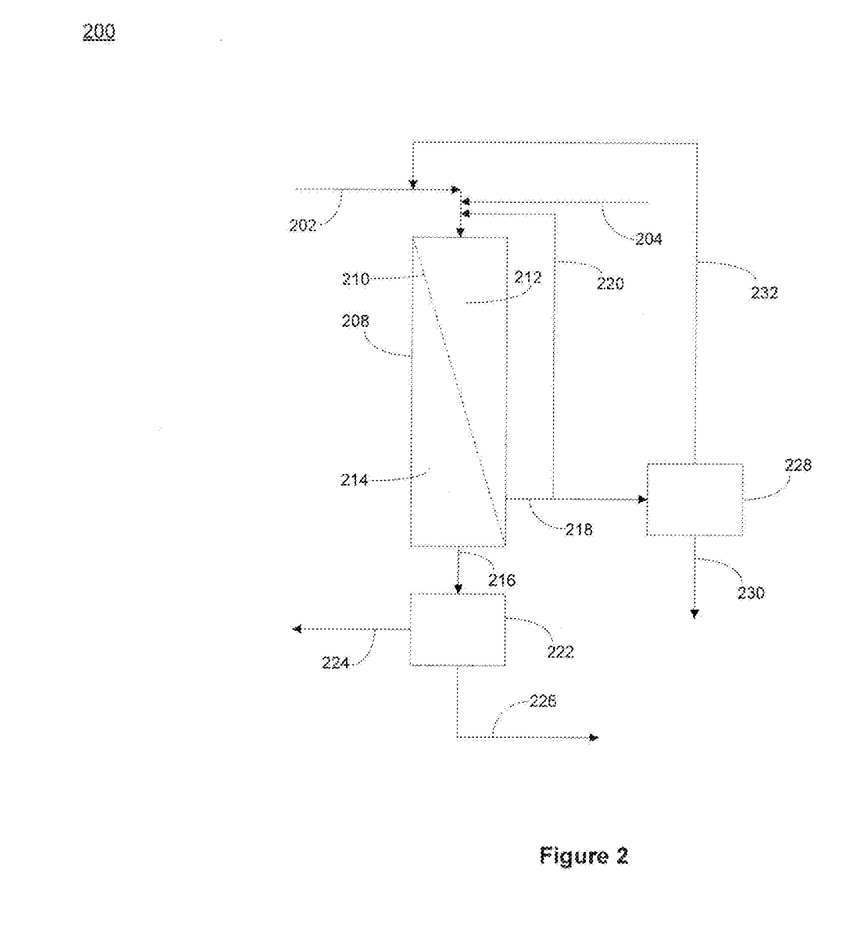
FIG. 2 provides a process diagram of one embodiment of the invention.

Referring now to FIG. 2, a process flow diagram of one embodiment of an integrated olefin hydration is provided. A mixed olefin feed stream is supplied to reactor 208 via line 202. Water is supplied via line 204 and combined with mixed olefin feed line 202 before the two are supplied as a single stream to hydration reactor 208. In certain embodiments, a mixing device may be utilized to provide sufficient mixing between the water and mixed olefin feed streams. Various recycle streams, as described below can also be combined with the mixed olefin feed stream. Hydration reactor 208 includes selective membrane 210, which serves to separate alcohols that are produced within the reactor from the mixed olefin feedstock, providing a permeate side 214 of the membrane, which includes alcohols that have passed through the membrane, and a retentate side 212 of the membrane, which includes water and mixed olefins that are not able to pass through the membrane. Hydration reactor 208 is packed with a solid catalyst and includes alcohol selective membrane 210. A retentate stream, which generally includes water and unreacted mixed olefin, as well as possibly including a minor amount of alcohol, is removed from the retentate side 212 of membrane 210 via line 218. Line 218 can optionally be supplied to recycle line 220, and combined with mixed olefin feed stream 202. Preferably, the retentate stream has a very low concentration of alcohol. At least a portion of the retentate stream can be supplied via line 218 to separator 228, which produces a mixed olefin recycle stream, which can be supplied via line 232 and combined with the mixed olefin feed stream in line 202. A stream that includes water and alcohol can be supplied form separator 228 via line 230 for further separation into alcohol and water streams. Water can be recycled to the reactor as needed. A permeate stream, which can include a minor amount of unreacted mixed olefins, is removed from the permeate side 214 of membrane 210 via line 216 and supplied to product separator 222. Product separator 222 produces an alcohol-rich product stream that is removed via line 226 and a mixed olefin stream that is removed via line 224. The alcohol-rich stream removed from product separator 222 via line 226 can be supplied to further purification processes, as desired. Mixed olefin stream 224 can be recycled to the reactor as desired.

Figure 3:
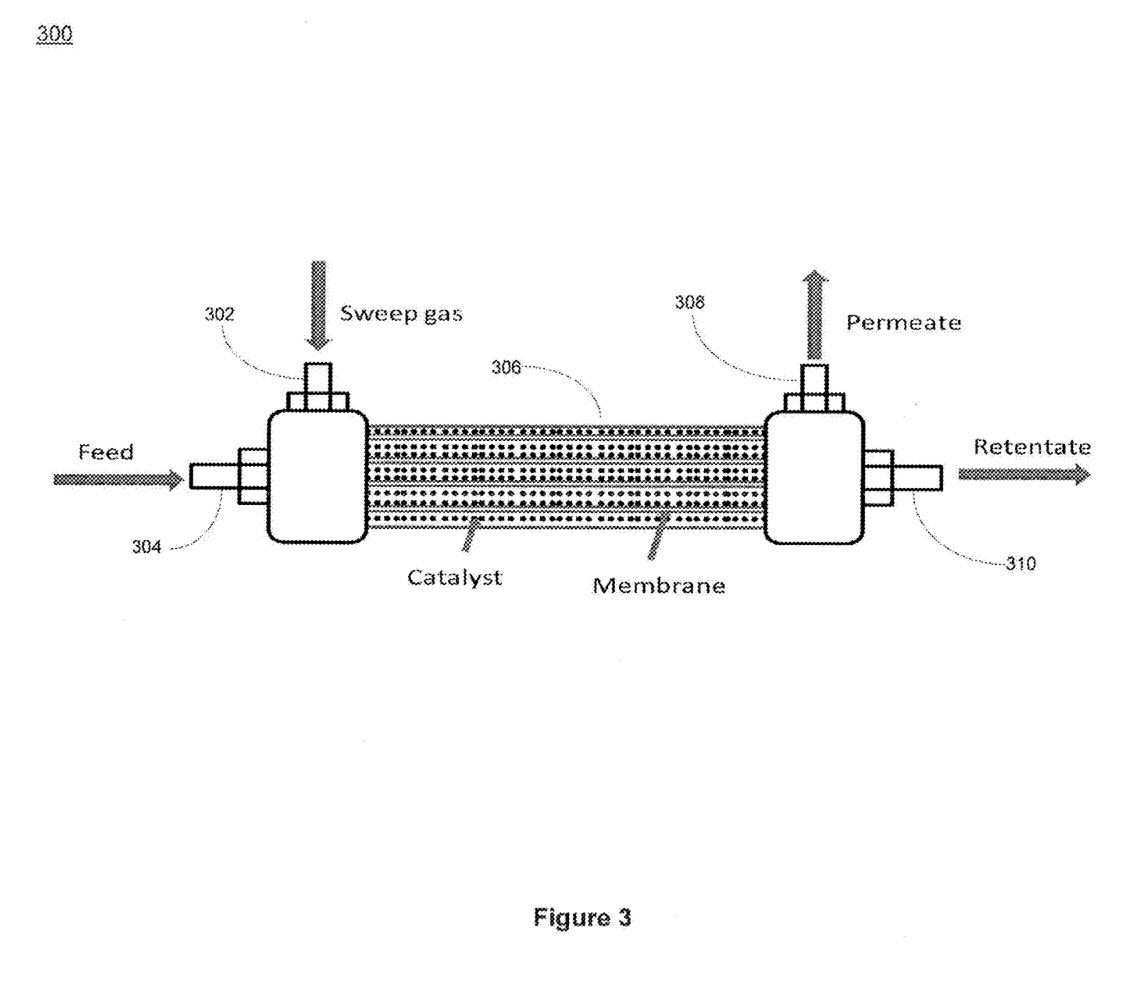
FIG. 3 provides the cross sectional view of one embodiment of the reactor.

FIG. 3 shows an embodiment of the reactor. Reactor 300, as shown, can be a cylindrical tube having an inlet section at one end, an outlet section at the other end, and a reaction zone positioned between the inlet and outlet sections of the reactor. A sweep gas, such as nitrogen, argon, helium, or other inert gas, can be supplied to reactor inlet 302 where the gas contacts a feed stream that includes water and olefins that is supplied to the reactor via inlet 304. An optional mixing device can be used to mix the two components. Reactor 300 includes reaction zone 306, positioned between the inlet and outlet ends of the reactor which includes catalyst for facilitating the reaction, and a membrane that is selective for the removal of alcohol from the catalyst. As noted above, a permeate that includes a major portion of the alcohol, and minor amount of water and/or unreacted mixed olefin feedstock can be removed via permeate outlet 308 and a retentate stream that includes water and/or unreacted mixed olefin feedstock, and a minor amount of alcohol, can be removed from reactor 300 via retentate outlet 310. In certain embodiments, a vacuum pump can be employed to maintain a low pressure on the permeate side of the membrane reactor.

Figure 4:
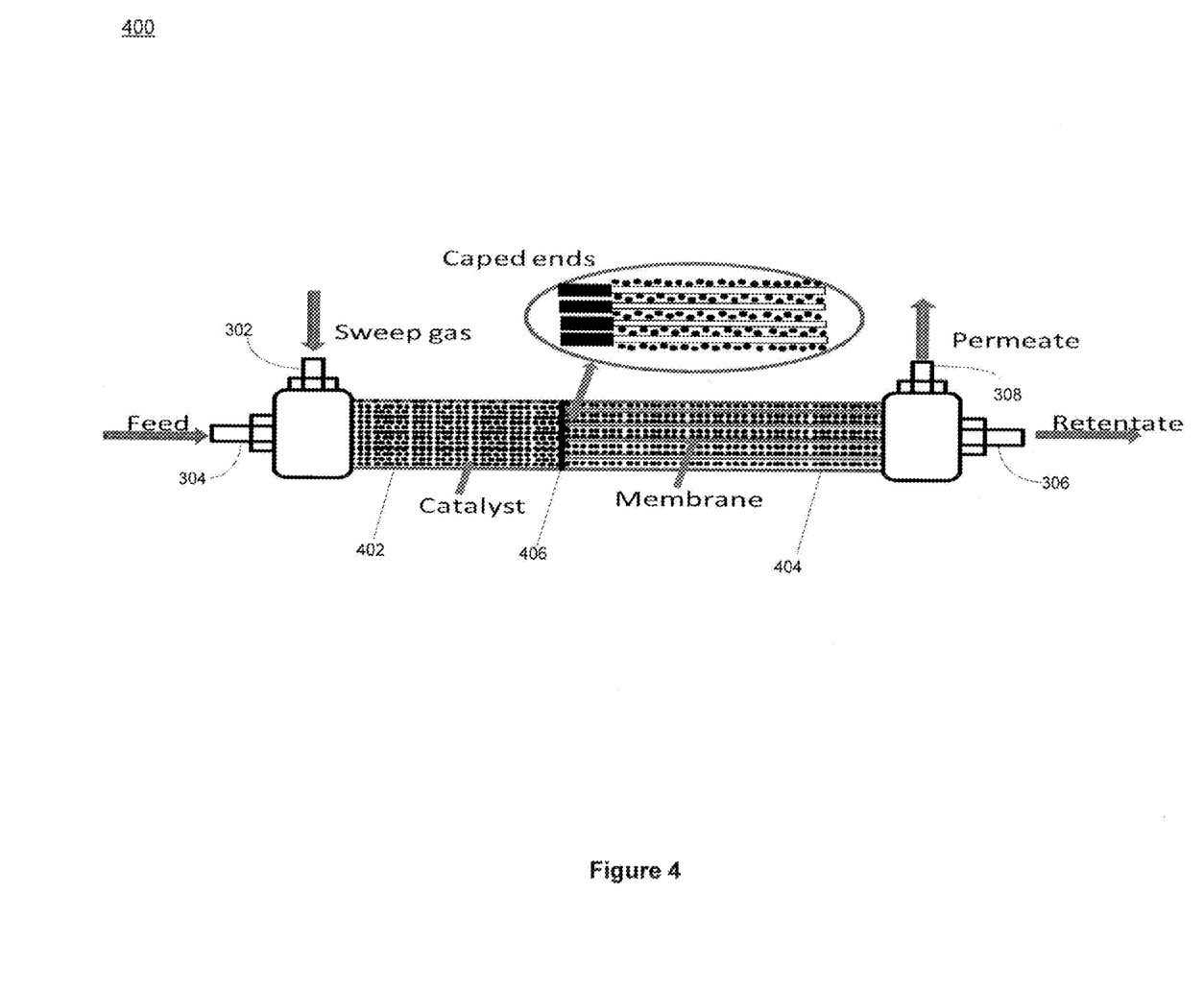
FIG. 4 provides the cross sectional view of one embodiment of the reactor.

Referring now to FIG. 4, in certain embodiments reactor 400, having a structure similar to the reactor provided in FIG. 3, can include multi-tube packed bed reactors that still include selective permeability membranes. The reaction chamber of the reactor can include a first catalyst bed 402 that includes packed catalyst, and which does not include any membranes, and a second catalyst bed 404 that includes one or more membrane tubes, wherein the tubes include a selective membrane. In certain embodiments, the selective membrane facilitates the passage of certain organic compounds, such as alcohols, while not allowing other compounds, such as water or olefins, to pass therethrough. The permeate, which includes alcohols that have passed through the selective membrane, can be collected via permeate outlet 308, and the retentate, which can include water and other compounds that do not readily pass through the membrane, can be collected via retentate outlet 310.

The catalyst selected for use in the reactors described herein can be any commercially available hydration catalyst. Exemplary catalysts can include water soluble catalyst, such as $H_2SO_4$ or $H_3PO_4$, or poly-heteroacids, or in certain embodiments can be a water insoluble catalyst, such as acidic zeolites, $MoO_3/WO_3$, ion exchange resins, or an acid that is supported on a carrier, such as silica, metal oxides, clays, zeolites, carbon black, and the like. Spent catalyst can be either regenerated or removed from the reactor and replaced.

While FIG. 1, as shown, illustrates the counter-current flow of the olefin and water into the reactor, which may provide improved mixing of the reactants, it is understood that within the scope of the invention includes the co-current flow of the reactants. For example, FIGS. 3 and 4 illustrate co-current flow of the water and olefin reactants.

EXAMPLES

The membrane separation of various liquids was tested using a membrane testing apparatus. The apparatus consists of two parallel test cells, for example, having an effective membrane area of about 3.7 $cm^3$ each. The feed can be circulated with a pump, for example, a centrifugal pump. An immersion heating circulator with a microprocessor control and a stainless steel bath, for example having an internal volume of about 6 L, were used to keep the feed at the desired temperature. Heating elements can be placed on top of the permeate vessels to prevent freezing of the pipelines. A medium vacuum can be maintained at the permeate side of the apparatus with a rotary pump that can be monitored on a thermovac system. The membrane can be placed into test cells, having an exemplary diameter of about 25 mm, and sealed with o-rings.

Example 1

A feedstock for characterizing separation for butanol that includes n-heptane, sec-butanol, tert-butanol, and water having the approximate composition provided in Table 1 was supplied to the reactor described above.

TABLE 1

| | Composition | | |
|---|---|---|---|
| Component | Weight % | Volume % | Mol % |
| n-heptane | 16.96 | 21.08 | 5.28 |
| Sec-butanol | 18.75 | 19.78 | 7.89 |
| Tert-butanol | 18.75 | 20.42 | 7.89 |
| Water | 45.54 | 38.72 | 78.93 |

The composition was flowed to the membrane testing apparatus at a pressure of about 2.8 bar and a temperature of about either 70° C. or 90° C. Four different semi-permeable membranes were tested, including alcohol-selective PUL-A1_M1 (Poly-an, Germany), hydrophobic PERVAP4060 (Sulzer Chemtech). WTA 303 and 5I-15130 (VITO Institute, Belgium), consisting of a thin poly(1-trimethylsilyl-1-propyne) (PTMSP) separating layer on top of a porous support. Membrane flux data for the experiment, for each different semi-permeable membrane, is provided in Table 2.

Membrane flux data for the feedstock provided in Table 1, as supplied to the exemplary device described herein, is provided in Table 2. As can be seen in Table 2, flow of the feedstock varies based on the selected membrane and temperature.

TABLE 2

| | | Flux ($kg/m^2h$) | | |
|---|---|---|---|---|
| Membrane | T (° C.) | Left | Right | Average |
| POL_AL_M1 | 70 | 8.57 | 7.9 | 8.24 |
| POL_AL_M1 | 90 | 14.95 | 14.55 | 14.75 |
| Pervap 4060 | 70 | 46.54 | 49.71 | 48.13 |
| Pervap 4060 | 90 | 67.43 | 64.89 | 66.16 |

TABLE 2-continued

| Membrane | T (° C.) | Flux (kg/m²h) | | |
|---|---|---|---|---|
| | | Left | Right | Average |
| 5I 15130 | 70 | 70.66 | 76.05 | 73.36 |
| 5I 15130 | 90 | 101.36 | 99.62 | 100.34 |
| WTA 303 | 70 | 32.43 | 32.33 | 32.38 |
| WTA 303 | 90 | 46.65 | 48.12 | 47.39 |

Membrane characterization data for the four different membranes tested at temperatures of 70° C. and 90° C. are provided in Table 3, below.

Permeate fluxes J (kg·m-2·h-1) were determined by following formula: wherein m, A and t represent the mass of the collected permeate, the active membrane surface area and the permeate collection time, respectively.

$$J = \frac{m}{A * t}$$

The composition of the different samples were used to calculate the selectivities of each of the tested membranes, either expressed by means of the separation factor αa/b or by means of the enrichment factor βa as defined below: wherein, Y denotes the concentrations (wt %) of the components a and h (e.g. sec. butanol and water) in the permeate, and X the same concentrations in the feed mixture.

Separation factor:

$$\alpha \frac{a}{b} = \frac{Y_a}{Y_b} * \frac{X_b}{x_2}$$

Enrichment factor:

$$\beta_a = \frac{Y_a}{X_a}$$

An ideal membrane will have high separation factor and high enrichment factor for alcohol. In the four membranes tested here the PTMSP based 5I-15130 has the highest separation and enrichment factor for butanols. Separation factor and enrichment factor increases with temperature for 5I-15130

Example 2

Composition data for 3 exemplary feedstock streams that include sec-butanol, tert-butanol and water is provided in Table 4, each having increasing concentrations of water.

TABLE 4

| Component | Stream I | | | Stream II | | | Stream III | | |
|---|---|---|---|---|---|---|---|---|---|
| | wt % | vol % | mol % | wt % | vol % | mol % | wt % | vol % | mol % |
| sec-butanol | 44.6 | 44.9 | 33.3 | 22.6 | 25.1 | 8.3 | 7.1 | 8.5 | 1.9 |
| tert-butanol | 44.6 | 46.3 | 33.3 | 22.6 | 25.9 | 8.3 | 7.1 | 8.7 | 1.9 |
| water | 10.8 | 8.8 | 33.3 | 54.6 | 49.0 | 83.4 | 85.8 | 82.8 | 96.2 |

The feedstock provided in Table 4 is supplied to a membrane testing apparatus, as described above, at temperatures of 70° C. and 90° C. Flux data for the three exemplary streams are provided below. Shown in Table 5 is the test data for various compositions for separation utilizing the WTA 303 membrane.

TABLE 5

| Stream | T (° C.) | Flux (kg/m²h) | | |
|---|---|---|---|---|
| | | Left | Right | Average |
| Stream I | 70 | 43.27 | 38.63 | 36.45 |
| | 90 | 48.21 | 50.13 | 49.17 |
| Stream II | 70 | 25.45 | 25.15 | 24.3 |
| | 90 | 38.21 | 38.86 | 38.54 |
| Stream III | 70 | 22.34 | 16.9 | 19.62 |
| | 90 | 28.98 | 22.97 | 27.48 |

Separation data for each of the 4 exemplary membranes is provided in Table 6, showing average separation and enrichment factors (based on two parallel measurements) of the four membranes. The PTMSP membranes are the most alcohol selective for this particular tert-butanol/sec-butanol/water feed mixture (Stream 11). The 5I-15130 membrane shows similar selectivity for sec-butanol and tert-butanol.

TABLE 3

| Membrane | T (° C.) | Separation Factor | | | | Enrichment Factor | | | |
|---|---|---|---|---|---|---|---|---|---|
| | | $\alpha_{heptane/water}$ | $\alpha_{tert-BuOH/water}$ | $\alpha_{sec-BuOH/water}$ | $\alpha_{alcohols/water}$ | $\beta_{heptane/water}$ | $\beta_{tert-BuOH/water}$ | $\beta_{sec-BuOH/water}$ | $\beta_{alcohols/water}$ |
| POL__AL__M1 | 70 | 0.3 | 2.83 | 3.5 | 2.82 | 0.23 | 2.12 | 2.62 | 2.12 |
| POL__AL__M1 | 90 | 1.51 | 2.62 | 3.15 | 2.73 | 1.16 | 2.02 | 2.43 | 2.1 |
| Pervap 4060 | 70 | 1.5 | 1.82 | 1.51 | 1.6 | 1.07 | 1.3 | 1.08 | 1.15 |
| Pervap 4060 | 90 | 4.07 | 2.85 | 2.56 | 3.1 | 1.67 | 1.19 | 1.06 | 1.28 |
| 5I 15130 | 70 | 3.14 | 7.4 | 9.88 | 7.84 | 1.53 | 3.61 | 4.82 | 3.82 |
| 5I 15130 | 90 | 27.46 | 10.12 | 15.3 | 14.45 | 9.03 | 3.27 | 4.95 | 4.7 |
| WTA 303 | 70 | 0.33 | 4.0 | 4.44 | 3.02 | 0.15 | 1.79 | 1.99 | 1.36 |
| WTA 303 | 90 | 2.71 | 3.17 | 3.83 | 3.27 | 1.16 | 1.32 | 1.6 | 1.38 |

TABLE 6

| Membrane | T (° C.) | Separation Factor | | | Enrichment Factor | | |
|---|---|---|---|---|---|---|---|
| | | $\alpha_{tert\text{-}BuOH/water}$ | $\alpha_{sec\text{-}BuOH/water}$ | $\alpha_{alcohols/water}$ | $\alpha_{tert\text{-}BuOH/water}$ | $\alpha_{sec\text{-}BuOH/water}$ | $\alpha_{alcohols/water}$ |
| POL_AL_M1 | 70 | 0.35 | 0.47 | 0.41 | 0.47 | 0.65 | 0.57 |
| POL_AL_M1 | 90 | 0.65 | 0.78 | 0.72 | 0.74 | 0.89 | 0.82 |
| Pervap 4060 | 70 | 0.96 | 1.05 | 1.01 | 0.96 | 1.04 | 1.00 |
| Pervap 4060 | 90 | 1.45 | 0.26 | 0.83 | 1.57 | 0.28 | 0.89 |
| 5I 15130 | 70 | 3.81 | 3.86 | 3.84 | 1.73 | 1.72 | 1.73 |
| 5I 15130 | 90 | 2.3 | 2.94 | 2.64 | 1.35 | 1.72 | 1.55 |
| WTA 303 | 70 | 1.37 | 0.25 | 0.79 | 1.49 | 0.27 | 0.86 |
| WTA 303 | 90 | 2.5 | 3.6 | 3.08 | 1.39 | 2.0 | 1.71 |

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these references contradict the statements made herein.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more reactants. It is to be understood that the words "first" and "second" serve no other purpose and are not part of the name or description of the reactant. Furthermore, it is to be understood that that the mere use of the term "first" and "second" does not require that there be any "third" or further reactant, although that possibility is contemplated under the scope of the present invention.

That which is claimed is:

1. A process for the hydration of olefins to produce alcohols, the process comprising the steps of:
    contacting an introduced olefin feedstock and an introduced water in a reaction zone at reaction conditions sufficient to produce an alcohol product, wherein said reaction zone includes a solid olefin hydration catalyst; and
    selectively removing at least a portion of the alcohol product from the reaction zone with a permeable membrane that is selective for the passage of alcohols, wherein the step of removing a portion of the alcohol product shifts the reaction equilibrium,
    where the olefin feedstock and the water upon introduction do not contain an acid catalyst,
    where the permeable membrane has a separation factor and an enrichment factor for tert-butanol, sec-butanol and mixed butanols, and
    where the permeable membrane has both a separation factor and an enrichment factor for each of tert-butanol, sec-butanol and mixed butanols, and each factor is greater than 1.0.

2. The process of claim 1, wherein the hydration of olefins to produce alcohols occurs in the reactor, the reactor comprising:
    the reaction zone separated by the permeable membrane, the permeable membrane separating the reaction zone into permeate and retentate sides of the reaction zone, where the retentate side contains the solid olefin hydration catalyst;
    a first outlet operable to pass permeate fluid from the permeate side of the reaction zone; and
    a second outlet operable to pass retentate fluids from the retentate side of the reaction zone;
    wherein the permeable membrane is operable to selectively remove at least one olefin hydration product.

3. The process of claim 1, wherein the olefin is selected from an olefin having between 2 and 6 carbon atoms.

4. The process of claim 1, wherein the olefin is selected from an olefin having between 3 and 5 carbon atoms.

5. The process of claim 1 where the selectively removing step occurs at a temperature in a range of from about 70° C. to about 90° C. and a pressure of about 2.8 bars.

6. The process of claim 1 where the selective removing step occurs such that such that permeate fluxes through the permeable membrane at an average flux rate in a range of from about 60 to about 110 kg/m²h.

7. The process of claim 1 where the selective removing step occurs such that the pressure on the permeate side of the permeable membrane is maintained at a pressure less than atmospheric.

8. The process of claim 1 where the selective removing step occurs such that the separation factor of tert-butanol to water is maintained across the permeable membrane in a range of from about 1 to about 11.

9. The process of claim 1 where the selective removing step occurs such that the separation factor of sec-butanol to water is maintained across the permeable membrane in a range of from about 1 to about 16.

10. The process of claim 1 where the selective removing step occurs such that the separation factor of mixed butanols to water is maintained across the permeable membrane in a range of from about 1 to about 15.

11. The process of claim 1 where the selective removing step occurs such that the enrichment factor of tert-butanol to water is maintained across the permeable membrane in a range of from about 1 to about 4.

12. The process of claim 1 where the selective removing step occurs such that the enrichment factor of sec-butanol to water is maintained across the permeable membrane in a range of from about 1 to about 5.

13. The process of claim 1 where the selective removing step occurs such that the enrichment factor of mixed butanols to water is maintained across the permeable membrane in a range of from about 1 to about 5.

14. The process of claim 1 where the contacting an olefin feedstock and water step further comprises contacting the olefin feedstock and water with a sweeping gas in the reaction zone at reaction conditions sufficient to produce the alcohol product.

15. The process of claim 14 where the sweeping gas is selected from the group consisting of nitrogen, argon, helium and combinations thereof.

16. The process of claim 1 where the hydration of olefins to produce alcohols occurs in the reactor, the reactor comprising:

a first reaction zone comprising a first solid olefin hydration catalyst and not comprising a permeable membrane;

a second reaction zone downstream from and fluidly coupled to the first reaction zone separated by the permeable membrane, the permeable membrane separating the second reaction zone into permeate and retentate sides of the second reaction zone, where the retentate side includes a second solid olefin hydration catalyst;

a first outlet operable to pass permeate fluid from the permeate side of the second reaction zone; and a second outlet operable to pass retentate fluid from the retentate side of the second reaction zone;

where the permeable membrane in the second reaction zone is operable to selectively remove at least one olefin hydration product.

* * * * *